(12) United States Patent
Wang

(10) Patent No.: US 8,328,770 B2
(45) Date of Patent: Dec. 11, 2012

(54) DISPOSABLE BLOOD TRANSFUSION DEVICE

(76) Inventor: Hsien-Tsung Wang, Taipei (TW)

( * ) Notice: Subject to any disclaimer, the term of this patent is extended or adjusted under 35 U.S.C. 154(b) by 70 days.

(21) Appl. No.: 12/986,249

(22) Filed: Jan. 7, 2011

(65) Prior Publication Data
US 2012/0179117 A1 Jul. 12, 2012

(51) Int. Cl.
*A61M 5/14* (2006.01)
(52) U.S. Cl. ........................ 604/254; 604/252; 137/430
(58) Field of Classification Search ...... 604/7, 251–256; 137/398, 399, 429, 430, 433; 222/66, 67, 222/181.1, 444, 453, 456, 571; 96/158, 168
See application file for complete search history.

(56) References Cited

U.S. PATENT DOCUMENTS

| | | | | |
|---|---|---|---|---|
| 2,784,733 A | * | 3/1957 | Martinez | 137/399 |
| 5,961,700 A | * | 10/1999 | Oliver | 96/158 |
| 6,569,116 B1 | | 5/2003 | Wang | |

* cited by examiner

*Primary Examiner* — Kevin C Sirmons
*Assistant Examiner* — Kami A Bosworth
(74) *Attorney, Agent, or Firm* — Jackson IPG PLLC

(57) ABSTRACT

One embodiment of a blood transfusion device includes a drip chamber (10) comprising a bottom outlet (113); a filter (40) fixedly disposed in the drip chamber (10); and a float regulator (20) moveably disposed in the drip chamber (10) under the filter (40), the float regulator (20) comprising an inverted upper cup (21) including a top projection (212), a lower cup (22) secured to the upper cup (21), and a suction cup (23) secured to an underside of the lower cup (22). An inner diameter of the upper cup (21) is greater than an outer diameter of the lower cup (22). The projection (212) contacts an underside of the filter (40) when blood from a blood bag (90) sufficiently fills the drip chamber (10). The suction cup (23) falls to permanently close the outlet (113) when blood in the drip chamber (10) completely drains.

4 Claims, 6 Drawing Sheets

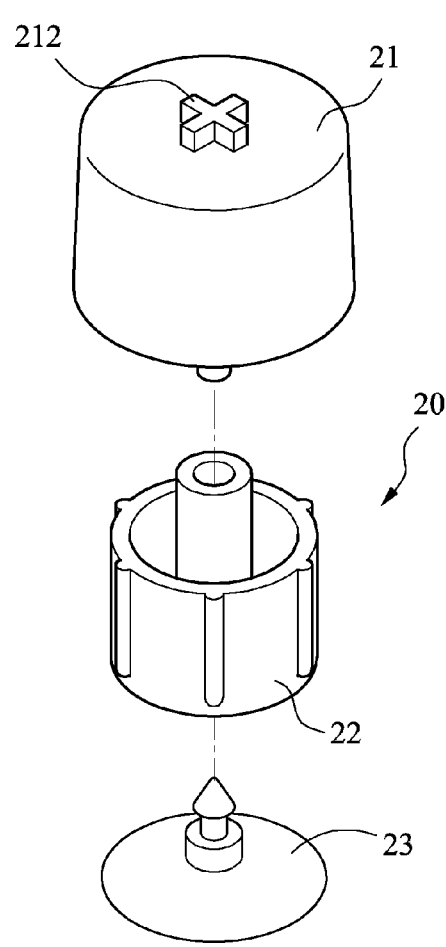
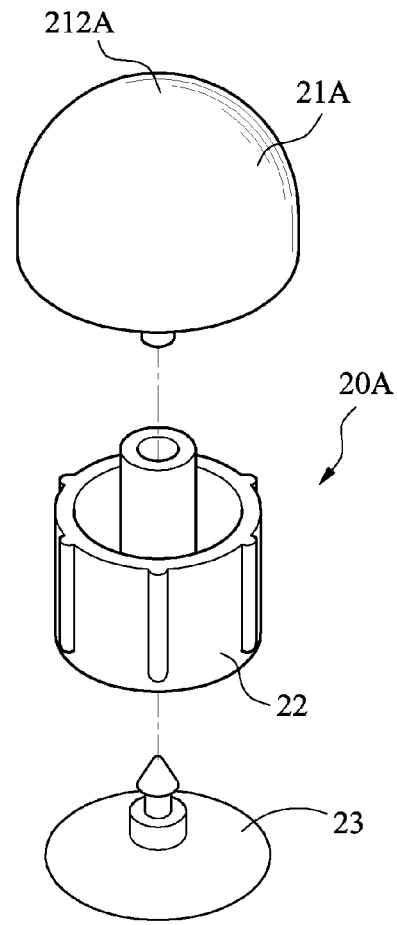
FIG.1
FIG.2
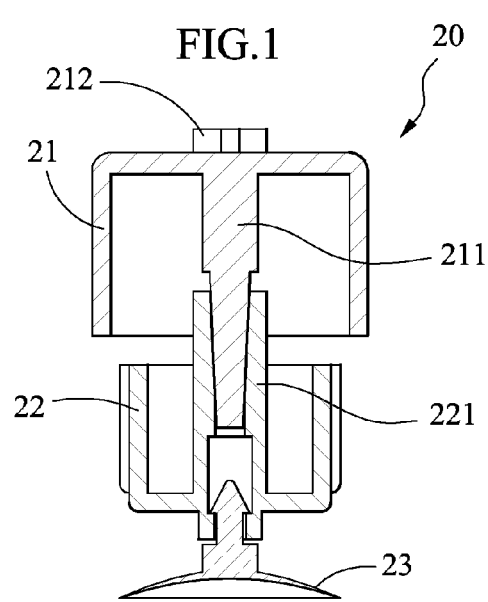
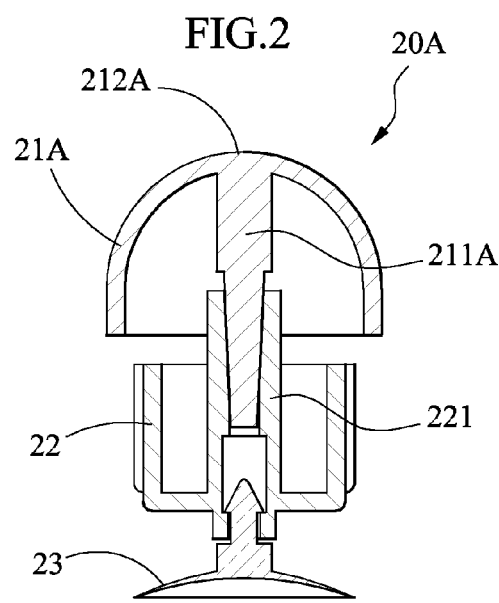
FIG.1A
FIG.2A

DISPOSABLE BLOOD TRANSFUSION DEVICE

BACKGROUND OF THE INVENTION

1. Field of Invention

The invention relates to blood transfusion devices and more particularly to a safety blood transfusion device which can be disposed after use.

2. Description of Related Art

U.S. Pat. No. 6,569,116 to Wang is directed to an intravenous (IV) flow controlling device comprising a flexible open container having a specific gravity less than one and an outer diameter smaller than that of the drip chamber, the container including a spherical bottom portion thinner than the shell upper portion thereof; a first plastic tube coupled to the bottom of the container being in communication with the exit; a flexible reservoir having one end coupled to the first tube; and a second plastic tube coupled to the other end of the reservoir being in communication therewith. The container is submerged as fluid filled in the drip chamber. Fluid flows through the exit, the first plastic tube, the reservoir, and the second plastic tube to cause the container to fall, thereby stopping fluid exiting when the bottom portion of the container closes the exit and fluid in the drip chamber is used up. The reservoir is capable of being squeezed to force solution stored in the reservoir to reverse flow through the first tube to disengage the container from the exit. The device functions normally when solution is used up, abnormal solution dropping, drip chamber shaken, or drip chamber slanted.

The patent works well when the source is saline. However, it is no appropriate for blood transfusion as detailed below. In blood transfusion, red cells, plasma and platelets are separated into different containers and stored in appropriate conditions so that their use can be adapted to a patient's specific needs. Red cells work as oxygen transporters, plasma is used as a supplement of coagulation factors, and platelets are transfused when their number is very scarce or their function severely impaired. Platelets in the blood may coagulate to form clots which can adversely block the small bores of the tubes. This in turn can cause the IV flow controlling device to fail. Thus, the need for improvement still exists.

SUMMARY OF THE INVENTION

It is therefore one object of the invention to provide a disposable safety blood transfusion device after use after considering the high viscosity of blood being liable to block the outlet of a typical drip chamber for IV infusion. Moreover, blood is prevented from entering a drip chamber of the blood transfusion device again via the outlet.

One aspect of the invention is to provide a disposable safety blood transfusion device in which contact between a filter and a float regulator is greatly decreased so as to prevent them from being adhered together. Otherwise, it may be uneasily separated due to the high viscosity of the blood after blood transfusion.

Another aspect of the invention is to provide a disposable safety blood transfusion device in which an outlet of a drip chamber is permanently closed by a suction cup after use. Thus, a second blood supply to the drip chamber via a blood bag cannot disengage the suction cup from the outlet even when blood accumulates in the drip chamber. Therefore, the blood transfusion device as well as the blood bag can be discarded.

By utilizing the invention, a number of advantages can be obtained as follows:

An inner diameter of an upper cup is slightly greater than an outer diameter of a lower cup and a float regulator is permitted to float between an outlet of a drip chamber and a filter in the drip chamber as blood fills the drip chamber from a blood bag.

Top of a float regulator is shaped as a cross, a curve, or any of other protrusions so as to effect a point contact rather than an area contact with a filter thereabove. Advantageously, it can prevent the float regulator from being uneasily disengaged from the filter once engaging because the viscosity of blood is higher than that of saline for IV infusion. It in turn can decrease the adherence of the float regulator to the filter. It is understood that it may malfunction the blood transfusion device if the float regulator and the filter become hard to separate after engaging.

A suction cup has a thicker sharp central portion and secured to a lower portion of a connector of a lower cup. The suction cup may permanently close the outlet of the drip chamber after use. Thus, a second blood supply to the drip chamber via a blood bag cannot disengage the suction cup from the outlet even when blood accumulates in the drip chamber. Therefore, the blood transfusion device as well as the blood bag can be discarded.

The above and other objects, features and advantages of the invention will become apparent from the following detailed description taken with the accompanying drawings.

BRIEF DESCRIPTION OF THE DRAWINGS

FIG. 1 is an exploded view of a float regulator of a drip chamber for a blood transfusion device according to a first preferred embodiment of the invention;

FIG. 1A is a longitudinal sectional view of the assembled float regulator of FIG. 1;

FIG. 2 is an exploded view of a float regulator of a drip chamber for a blood transfusion device according to a second preferred embodiment of the invention;

FIG. 2A is a longitudinal sectional view of the assembled float regulator of FIG. 2;

DETAILED DESCRIPTION OF THE INVENTION

Figure 3:
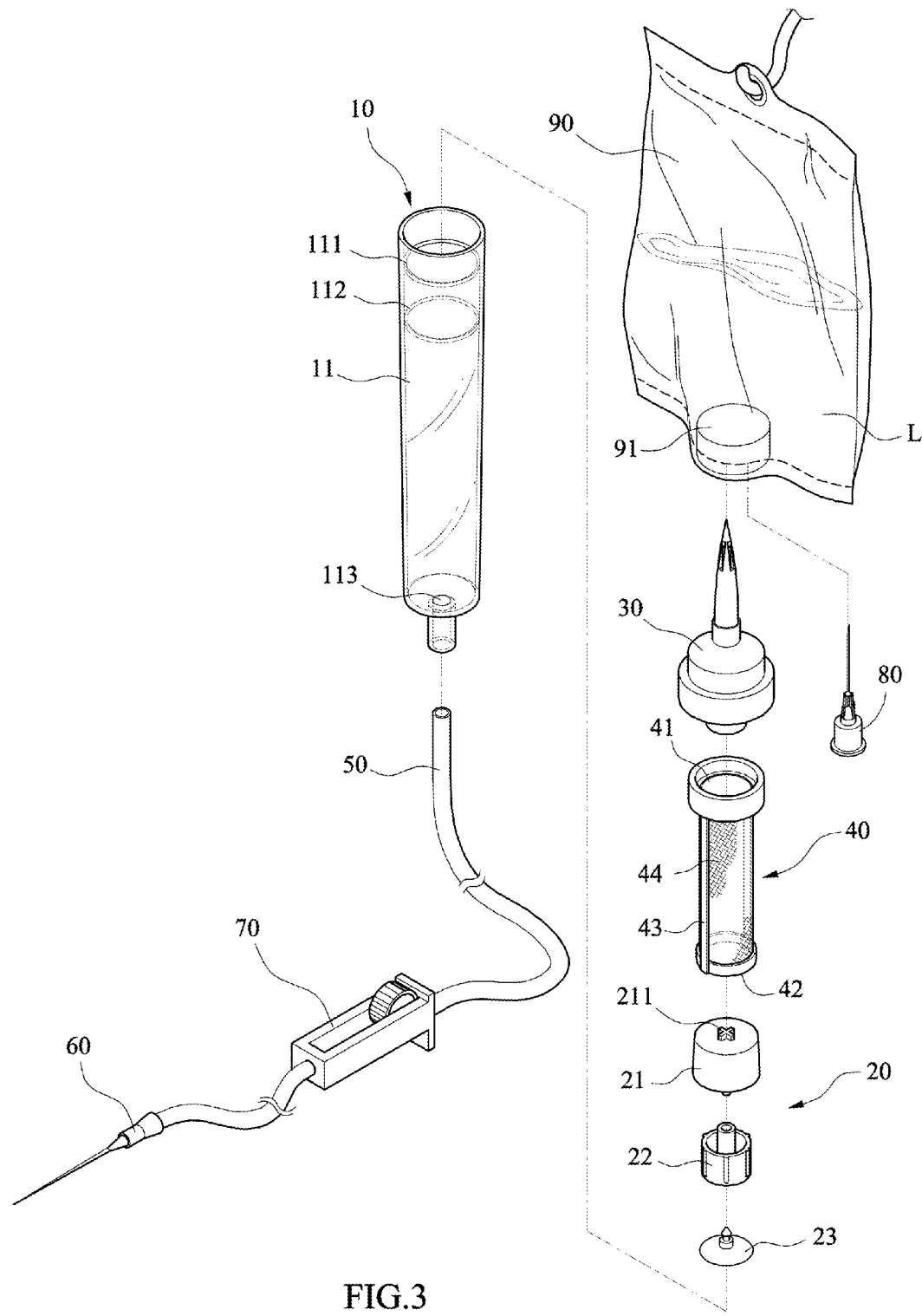
FIG. 3 is an exploded view of a blood transfusion device according to the first preferred embodiment of the invention and a blood bag to be assembled therewith.
Figure 4:
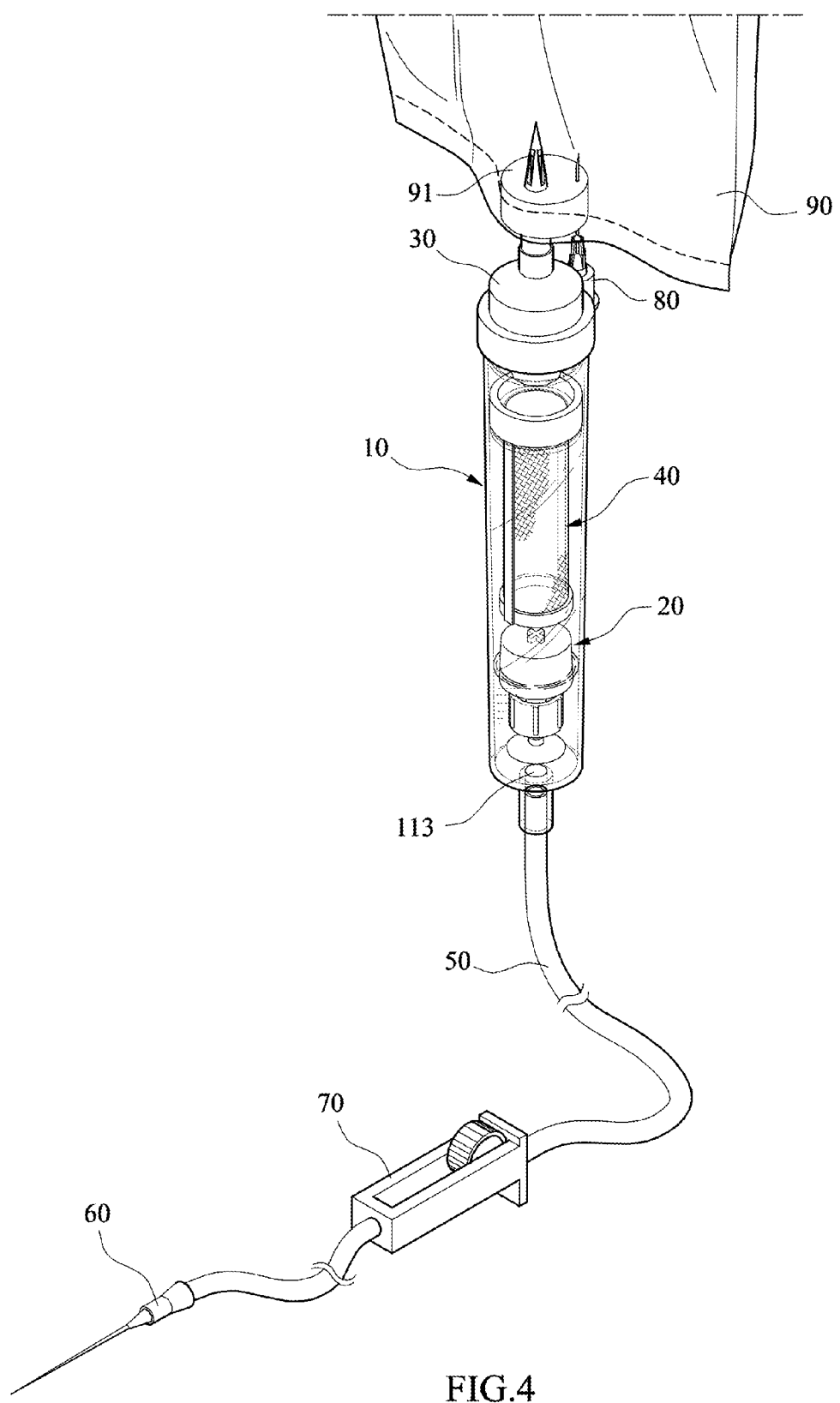
FIG. 4 is a perspective view of the assembled blood transfusion device and the blood bag.
Figure 5:
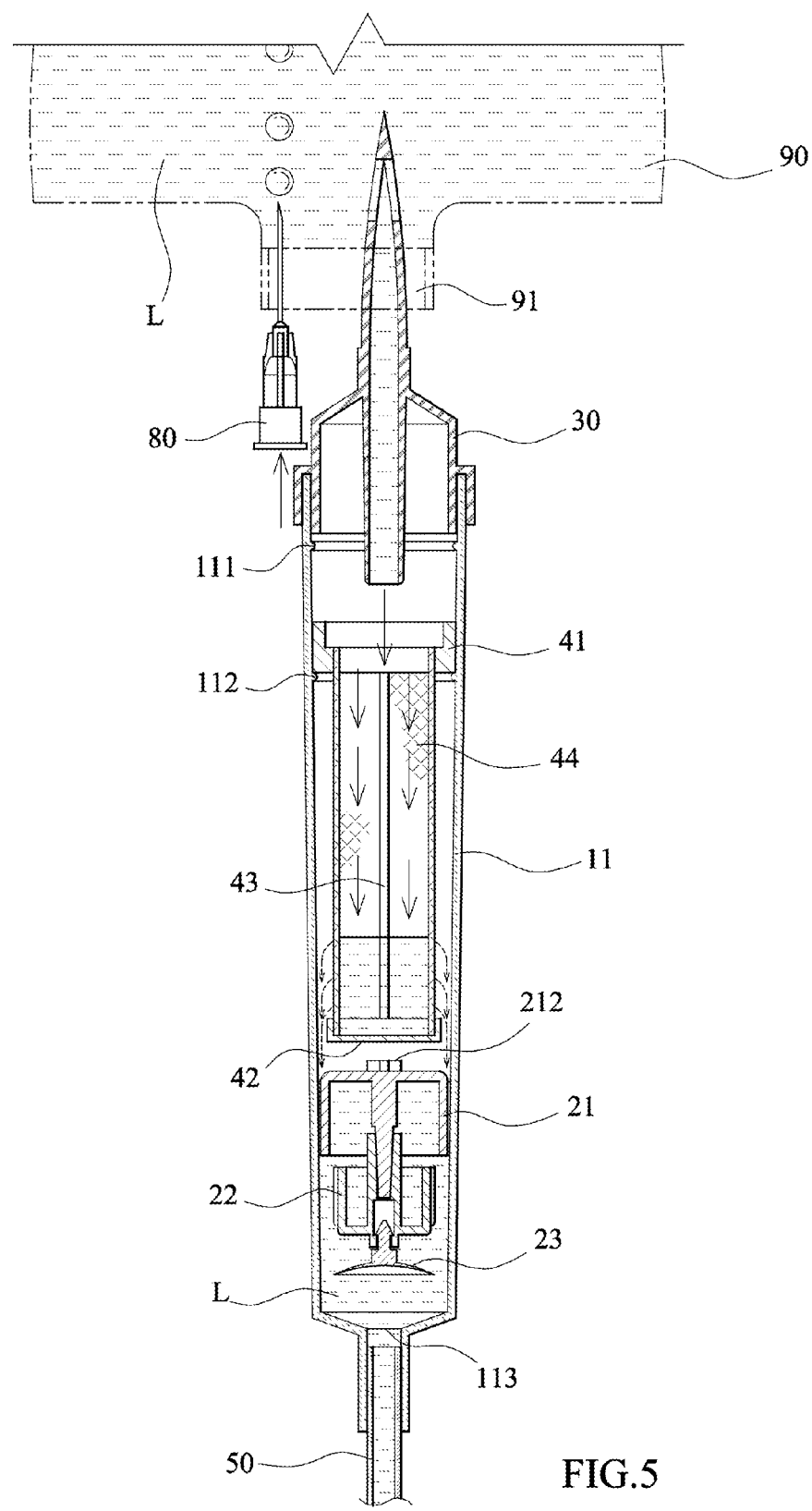
FIG. 5 is a longitudinal sectional view of the drip chamber and the blood bag of FIG. 4 where blood begins to flow into the drip chamber for blood transfusion.

Referring to FIGS. 1 and 1A, a float regulator 20 of a drip chamber for a blood transfusion device in accordance with a first preferred embodiment of the invention comprises the following components as discussed in detail below.

The float regulator 20 comprises an inverted cylindrical upper cup 21 including a cross shaped projection 212 on a top center, and a peg 211 extending downward from a bottom center directly under the projection 212; a cylindrical lower cup 22 including a hollow connector 221 through a bottom center for complimentarily securing to the peg 211; and a suction cup 23 having a thicker sharp central portion and secured to a lower portion of the connector 221. It is noted that the projection 212 may have other shapes in other preferred embodiments. An inner diameter of the upper cup 21 is slightly greater than an outer diameter of the lower cup 22.

Referring to FIGS. 2 and 2A, a float regulator 20A of a drip chamber for a blood transfusion device in accordance with a second preferred embodiment of the invention comprises the following components as discussed in detail below.

The float regulator 20A comprises an inverted substantially half spherical upper cup 21A including a curved top 212A and a peg 211A extending downward from a bottom center; a lower cup 22 including a hollow connector 221 through a bottom center for complimentarily securing to the peg 211A; and a suction cup 23 secured to a lower portion of the connector 221. An inner diameter of the upper cup 21A is slightly greater than an outer diameter of the lower cup 22.

Referring to FIGS. 3 to 8, a blood transfusion device in accordance with a first preferred embodiment of the invention comprises the following components as discussed in detail below.

A drip chamber 10 comprises a rigid transparent cylindrical casing 11 slightly tapered toward bottom, an annular first flange 111 proximate to a top open end, an annular second flange 112 under the first flange 111, and a cylindrical outlet 113 extending downward from a bottom center.

A pointed member 30 is adapted to pierce through a fixed bottom plug 91 of a blood bag 90 and mount on top of the drip chamber 10 by snappingly securing to the first flange 111. A needle 80 is adapted to pierce through the plug 91 to supply air into blood L stored in the blood bag 90.

A cylindrical filter 40 comprises a top mounting member 41 snappingly secured to the second flange 112, a bottom support 42, two opposite posts 43 provided between the mounting member 41 and the support 42, and a mesh structure 44 having a great number of closely-spaced holes, the mesh structure 44 disposed between the mounting member 41 and the support 42 with the posts 43 being disposed on the outer surface of the mesh structure 44. The filter 40 is disposed in the drip chamber 10 under the pointed member 30. The filter 40 is fixedly disposed above the float regulator 20 in an assembled state of the drip chamber 10 with the suction cup 23 closing the outlet 113 due to weight. Note that the outer diameter of the float regulator 20 is slightly smaller than an inner diameter of the drip chamber 10 so that the float regulator 20 may slidingly float in a portion of the drip chamber 10 under the filter 40.

An infusion tube 50 has one end connected to the outlet 113. A catheter 60 has its female fitting connected to the other end of the infusion tube 50. A manual flow control device 70 is mounted on the infusion tube 50 between both ends of the infusion tube 50.

An operation of the blood transfusion device will now be described. Blood L from the blood bag 90 begins to fill the drip chamber 10 via the pointed member 30 which pierces through the blood bag 90. Blood L then flows through the filter 40 with impurities being removed by the mesh structure 44. Next, blood L drops into the lower portion of the drip chamber 10 to accumulate therein and in both the upper cup 21 and the lower cup 22. The buoyancy of blood L accumulated in the drip chamber 10 is increased gradually to be greater than the weight of the float regulator 20. Therefore, the float regulator 20 begins to move upward to disengage from the outlet 113 to submerge in the drip chamber 10 (see FIG. 5).

Also, an amount of blood L leaves the drip chamber 10 and enters the infusion tube 50 to transmit to the catheter 60 which inserts into circulatory system of a patient. Thus, blood transfusion can be done. It is noted that the amount of blood transmitted to the patient can be regulated by the manual flow control device 70.

Figure 6:
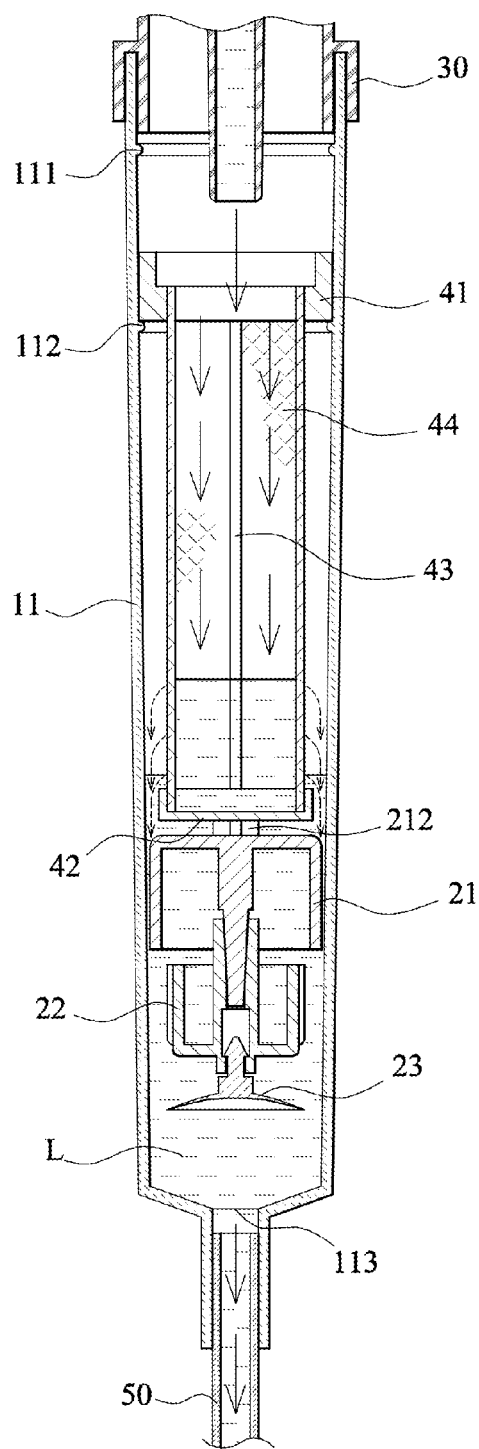
FIG. 6 is a longitudinal sectional view of the drip chamber of FIG. 5 where blood continues to flow into the drip chamber for blood transfusion.
Figure 7:
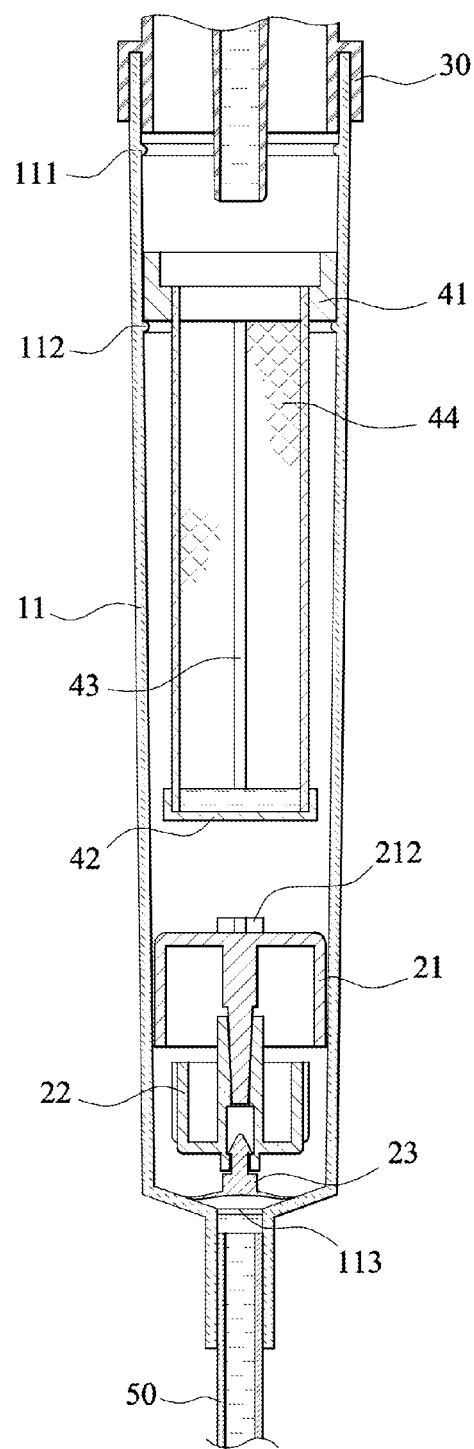
FIG. 7 is a view similar to FIG. 6 where blood stops flowing at the end of blood transfusion.

The upward movement of the float regulator 20 will be stopped when the projection 212 contacts the underside of the support 42 (see FIG. 6). That is, the contact between the float regulator 20 and the filter 40 is a point contact rather than an area contact. Advantageously, it can prevent the float regulator 20 from being uneasily disengaged from the filter 40 once engaging because the viscosity of blood is higher than that of saline for intravenous (IV) infusion and it in turn can decrease the adherence of the float regulator 20 to the filter 40 (i.e., the point contact can decrease the adherence).

To the contrary, the projection 212 may disengage from the filter 40 when the weight of the float regulator 20 is greater than the buoyancy of the blood L in the lower portion of the drip chamber 10 is decreased as the blood L continues to leave the drip chamber 10 with blood L in the blood bag 90 being used up. That is, the float regulator 20 begins to fall. Finally, the suction cup 23 closes the outlet 113 at the end of blood transfusion (see FIG. 7).

Figure 8:
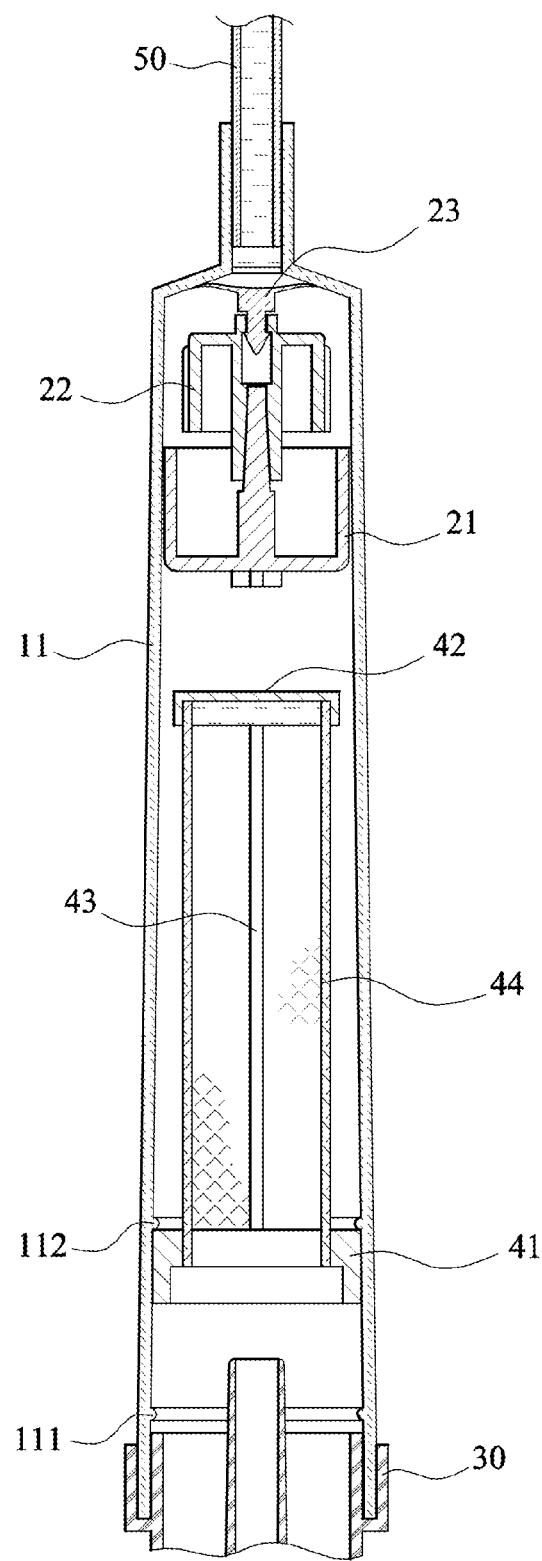
FIG. 8 is a longitudinal sectional view showing an inversion of the components shown in FIG. 7.

Advantageously, the closing of the outlet 113 is permanent as evidenced by inverting the drip chamber 10 (see FIG. 8). Thus, blood in the infusion tube 50 is prevented from entering the drip chamber 10 via the outlet 113. Also, a second blood supply to the drip chamber 10 via the blood bag 90 will not disengage the suction cup 23 from the outlet 113 even when blood accumulates in the drip chamber 10 as described in the previous paragraphs. Therefore, the blood transfusion device including the drip chamber 10, the float regulator 20, the pointed member 30, the filter 40, the infusion tube 50, the catheter 60, the manual flow control device 70, and the needle 80 as well as the blood bag 90 can be discarded after use (i.e., disposable).

Referring to FIGS. 2 and 2A in conjunction with FIGS. 3 to 8, the curved top 212A also has the effect of decreasing contact area of the float regulator 20 and the filter 40 (i.e., being point contact). Therefore, after blood transfusion, the closing of the outlet 113 by the suction cup 23 is permanent. Blood in the infusion tube 50 is prevented from entering the drip chamber 10 via the outlet 113. Also, a second blood supply to the drip chamber 10 via the blood bag 90 will not disengage the suction cup 23 from the outlet 113 even when blood accumulates in the drip chamber 10 as described with respect to the first preferred embodiment above. Therefore, the blood transfusion device including the drip chamber 10, the float regulator 20A, the pointed member 30, the filter 40, the infusion tube 50, the catheter 60, the manual flow control device 70, and the needle 80 as well as the blood bag 90 can be discarded after use (i.e., disposable).

While the invention has been described in terms of preferred embodiments, those skilled in the art will recognize that the invention can be practiced with modifications within the spirit and scope of the appended claims.

What is claimed is:

1. A blood transfusion device comprising:
a drip chamber (10) comprising a bottom outlet (113);
a filter (40) fixedly disposed in the drip chamber (10); and
a float regulator (20) moveably disposed in the drip chamber (10) under the filter (40), the float regulator (20) comprising an inverted upper cup (21) including a top projection (212), a lower cup (22) secured to the upper cup (21), and a suction cup (23) secured to an underside of the lower cup (22);
wherein an inner diameter of the upper cup (21) is greater than an outer diameter of the lower cup (22);

wherein the projection (212) is configured to contact an underside of the filter (40) when blood from a blood bag (90) sufficiently fills the drip chamber (10); and wherein the suction cup (23) is configured to fall to permanently close the outlet (113) when blood in the drip chamber (10) completely drains.

2. The blood transfusion device of claim 1, wherein the projection (212) is cross shaped.

3. The blood transfusion device of claim 1, wherein the upper cup (21) further comprises a peg (211) extending downward from a bottom center, and wherein the lower cup (22) comprises a hollow connector (221) through a bottom center complimentarily secured to the peg (211).

4. The blood transfusion device of claim 1, wherein the filter (40) is cylindrical and comprises a top mounting member (41), a bottom support (42), two opposite posts (43) disposed between the mounting member (41) and the support (42), and a mesh structure (44), disposed between the mounting member (41) and the support (42) with the posts (43) being disposed on an outer surface of the mesh structure (44).

\* \* \* \* \*